United States Patent
Schwer et al.

(10) Patent No.: US 8,986,350 B2
(45) Date of Patent: Mar. 24, 2015

(54) OSTEOSYNTHESIS PLATE

(75) Inventors: Stefan Schwer, Lorrach (DE); Eric Mariethoz, Haute-Nendaz (CH); Daniel Andermatt, Mohlin (CH); Olando Martinelli, Herzogenbuchsee (CH)

(73) Assignee: DePuy Synthes Products, Inc., Raynham, MA (US)

( * ) Notice: Subject to any disclaimer, the term of this patent is extended or adjusted under 35 U.S.C. 154(b) by 2122 days.

(21) Appl. No.: 11/628,286

(22) PCT Filed: Jun. 1, 2004

(86) PCT No.: PCT/IB2004/001784
§ 371 (c)(1),
(2), (4) Date: Aug. 22, 2007

(87) PCT Pub. No.: WO2005/117732
PCT Pub. Date: Dec. 15, 2005

(65) Prior Publication Data
US 2010/0069906 A1   Mar. 18, 2010

(51) Int. Cl.
*A61B 17/80* (2006.01)
(52) U.S. Cl.
CPC ............. *A61B 17/8061* (2013.01); *A61B 17/80* (2013.01)
USPC .......................................................... 606/280
(58) Field of Classification Search
USPC ................... 606/280, 283–284, 288–290, 295
See application file for complete search history.

(56) References Cited

U.S. PATENT DOCUMENTS

| 4,297,993 | A | 11/1981 | Härle |
| 5,785,712 | A | 7/1998 | Runciman et al. |
| 2001/0047172 | A1* | 11/2001 | Foley et al. ............... 606/69 |
| 2002/0045896 | A1* | 4/2002 | Michelson ............... 606/61 |

FOREIGN PATENT DOCUMENTS

| EP | 1486175 A2 | 12/2004 | | |
| WO | WO 98/51226 A2 | 11/1998 | | |
| WO | WO 9851226 | * 11/1998 | ............. | A61B 17/56 |
| WO | WO 9851226 A2 | * 11/1998 | ............. | A61B 17/56 |

OTHER PUBLICATIONS

E.J. Hearn, "Mechanics of Materials, Volume 2—The Mechanics of Elastic and Plastic Deformation of Solids and Structural Materials," 3d Edition, Elsevier, Amsterdam, 1997, pp. 410, 414, 429, 431, and 434.
Walter D. Pilkey, "Peterson's Stress Concentration Factors," 2d Edition, John Wiley & Sons, New York 1997, pp. 225, 239-241.
Synthes USA, "3.5mm LCP Proximal Humerus Plate," Dec. 2003, XP002315180, pp. 1, 5, 8, 9.

* cited by examiner

*Primary Examiner* — Christian Sevilla
(74) *Attorney, Agent, or Firm* — Fay Kaplun & Marcin, LLP

(57) ABSTRACT

An osteosynthesis plate includes at least two drilled holes arranged adjacent to one another. A notch is arranged on the convex side of the osteosynthesis plate, between the at least two drilled holes arranged adjacent to one another.

11 Claims, 2 Drawing Sheets

OSTEOSYNTHESIS PLATE

This application is a national stage application of PCT/IB2004/001784, filed Jun. 1, 2004.

FIELD OF THE INVENTION

The present invention relates to an osteosynthesis plate comprising a convex surface and a concave surface, at least two drilled holes arranged adjacent to each other, and a notch formed in the convex surface and extending toward, but not penetrating the concave surface. The invention relates in particular to an osteosynthesis plate for internal fixation of bone fragments.

BACKGROUND OF THE INVENTION

Osteosynthesis plates for implantation, anatomical reduction and internal splint fixation of bone fragments following bone fractures are known to a large extent in a very wide range of forms and developments. The success of fracture care is substantially determined by the stability of the implants. The stability is critical for ensuring healing of the fracture before failure of the implant. The stability should be as high as possible without the implant being excessively thick and hence too rigid. Excessive thickness of the implant could lead to a disturbance of the soft tissues. Furthermore, an implant which is comparatively stiff owing to an excessive thickness does not have the elasticity required for healing.

Osteosynthesis plates usually have a number of drilled holes through which bone screws for the fixation of the implants to the bone and hence for fixation of the fracture are passed. Particularly in the case of implants which are used in the articular region, frequently a plurality of drilled holes are arranged comparatively close together. Especially in the case of convex plates, this leads to a reduction of the stability in this region. The bearing cross-section is weakened there owing to the drilled holes. The region still remaining between the two drilled holes is firstly isolated and secondly is comparatively far away from the neutral fibres of the plate owing to the convex shape. Consequently, bending loads on the convex side result in an excessive stress, which could lead to failure of the plate precisely in this region. Thus, a comparatively small region is critical overall for the stability of an osteosynthesis plate. This may decide the success or failure of fracture care.

SUMMARY OF THE INVENTION

It is therefore an object of the present invention to improve the stability of osteosynthesis plates. In particular, it is intended to improve the stability of osteosynthesis plates where at least two drilled holes are comparatively close together.

This and other objects are achieved, according to the invention, by an osteosynthesis plate comprising at least two drilled holes arranged adjacent to one another, characterized in that at least one notch is arranged on the convex side of the osteosynthesis plate, between the at least two drilled holes arranged adjacent to one another.

An osteosynthesis plate according to the invention has at least two drilled holes arranged adjacent to one another. According to the invention, at least one notch is arranged between these two drilled holes. As mentioned above, excessive stresses occur under bending loads on the convex side in the case of drilled holes arranged adjacent to one another. At first glance, it therefore does not appear very advantageous to remove even further material from a point of maximum load. Surprisingly, however, the opposite is the case. By means of the at least one notch, it is ensured that stress peaks are eliminated and the maximum bending load is distributed over a broader web. Furthermore, a part of the load is conducted to the outside of the plate. The region on the outside of the drilled holes is usually substantially broader than the web remaining between the drilled holes. Consequently, this can also take up a greater load. Such a relief notch is considered to be advantageous especially in angularly-stable plate osteosynthesis, since the total load is borne by the plate in the case of angularly stable anchoring.

The prior art already discloses plates which have incisions or notches at certain points. Thus, firstly, undercuts are known. In this connection, the osteosynthesis plate is provided with notches on the underside, with the result that the contact area between plate and bone is reduced. This results in less disturbance of the periosteal blood supply, which improves healing. Furthermore, lateral incisions in reconstruction plates are known, where they ensure better flexibility of the plate perpendicular to the longitudinal direction. Without these incisions, there is the risk that the plate would bend only across the material weakened by the drilled hole, resulting in a change in the shape of the drilled hole, which may be disadvantageous in the case of fixation by means of a bone screw. What is important, however, is that all these notches and incisions are in particular not made in the immediate region or the immediate environment of drilled holes. The cross-sections in the region of the drilled holes would be weakened by above-mentioned incisions. Moreover, the distortion of the drilled holes by the bending of the plate can be prevented only by a correspondingly greater distance of the incisions from the drilled holes. Consequently, the known osteosynthesis plates, whether with or without known incisions, cannot contribute to the achievement of the object. None of the known incisions and notches leads to a distribution or deflection of the load away from the critical region between the drilled holes.

The list of reference numerals and the drawings, together with the articles described in the claims, are an integral part of this disclosure.

BRIEF DESCRIPTION OF THE DRAWINGS

The invention can be even better understood by reference to the attached exemplary figures. They are described in relation to one another and overall. Identical reference numerals denote identical components, and indices indicate functionally identical components.

DETAILED DESCRIPTION

Figure 1:
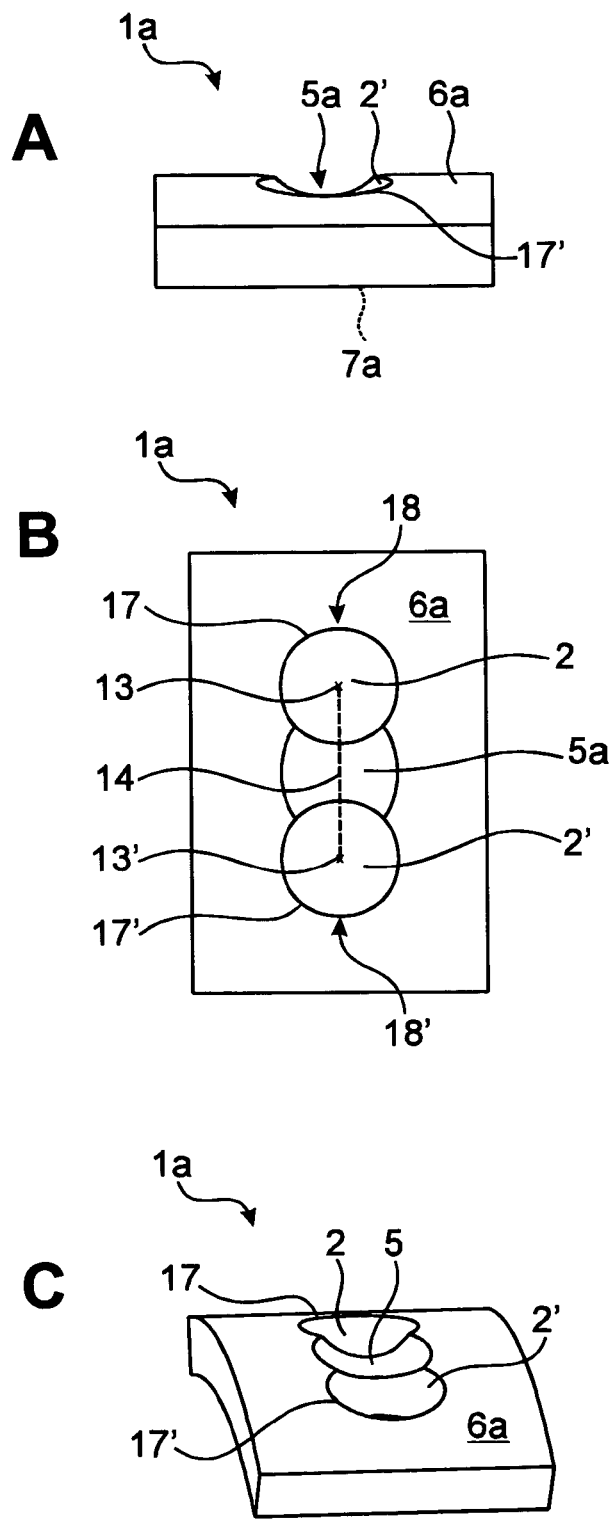
FIG. 1 shows a cut-out from a generic plate in side view (A), plan view (B) and perspective view (C)

FIG. 1 shows a cut-out from a generic plate 1a in various views. The generic plate is a model for an osteosynthesis plate, in order to illustrate the basic principle of the invention. The cut-out, shown in FIG. 1, of the generic plate 1a has two drilled holes 2, 2'. The two drilled holes 2, 2' pass through the plate so that a screw can be introduced. A notch 5a is arranged between the drilled holes 2, 2'. As is evident from the drawing of FIG. 1B, this notch 5a is present between the two drilled holes 2, 2'. In other words, the notch 5a links the two drilled holes 2, 2'; it runs from drilled hole 2 to drilled hole 2'. The generic plate 1a is an arched plate. It has a convex side 6a and a concave side 7a. As is evident in particular from FIG. 1C, the notch 5a is arranged in the convex side 6a. The concave side 7a remains unchanged.

Figure 2:
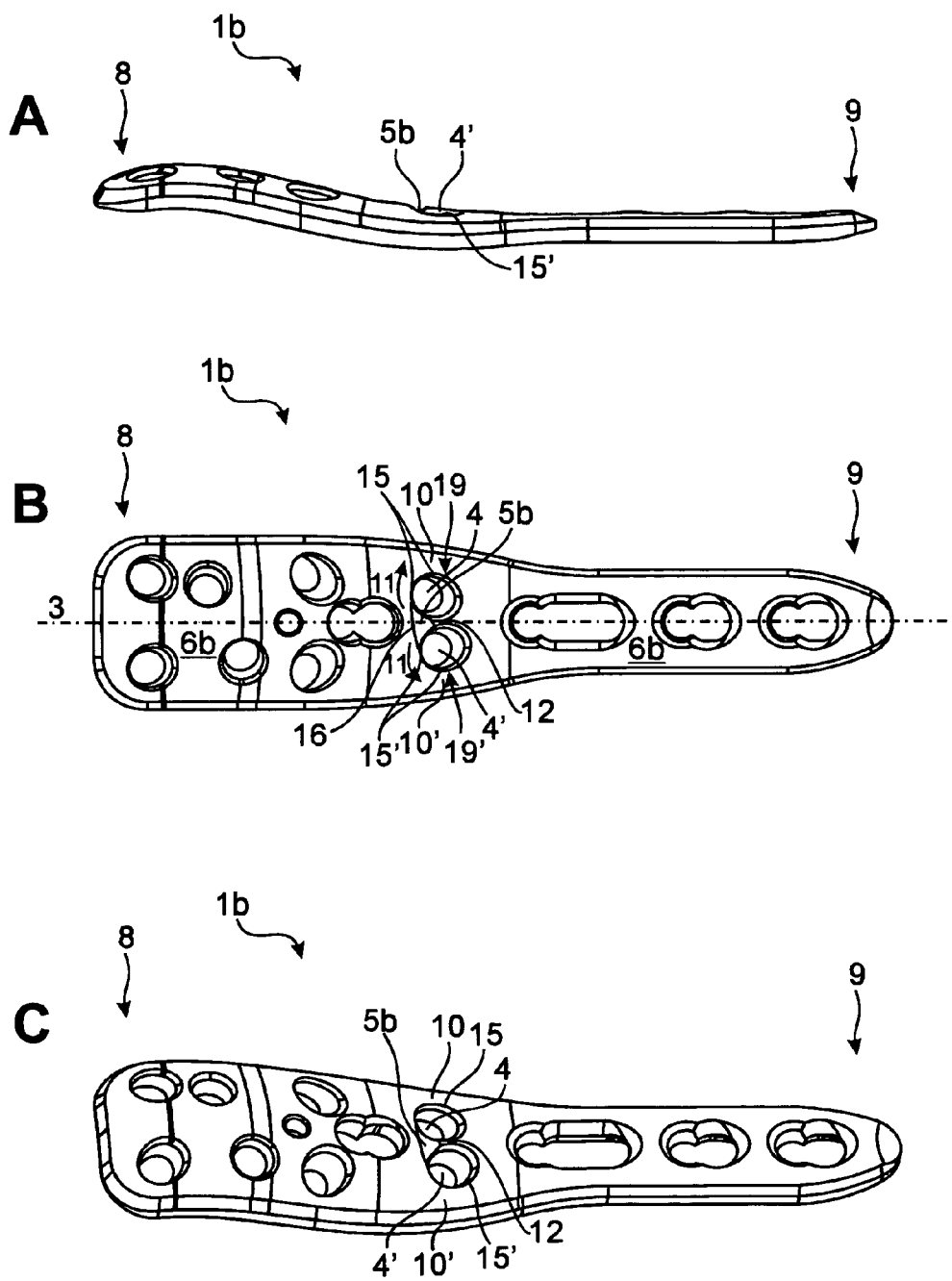
FIG. 2 shows an embodiment of an osteosynthesis plate in side view (A), plan view (B) and perspective view (C).

FIG. 2 shows an osteosynthesis plate 1b in various views. The osteosynthesis plate 1b has different types of drilled holes. The term "drilled hole" is understood herein as meaning any orifice or bore in the plate according to the invention through which means for fixing the plate with and to a bone can be introduced. Thus, for example, both cylindrical and conical drilled holes as well as slots and drilled holes having a thread, and combinations thereof, are included therein. As is evident from FIG. 2, the two drilled holes 4, 4' in the middle region of the osteosynthesis plate 1b are arranged comparatively close together. In the region of the two drilled holes 4, 4', an excessive stress occurs under bending load on the convex side 6b, as mentioned above. According to the invention, a notch 5b extends between these drilled holes 4, 4'. By making the notch 5b, the load which rests on the web 12 in the region between the two drilled holes 4, 4' is more uniformly distributed, for example deflected to the lateral webs 10, 10', as indicated by the arrows 11. Particularly from the diagram of FIG. 2B, it is clear that the lateral webs 10, 10' are broader than the middle web 12. Consequently, the web 10, 10' can also take up a greater load than the web 12. Moreover, the area moment of inertia here is reduced only slightly by making the notch 5b, at the same time the extreme fibre spacing being disproportionately shortened. This makes a substantial contribution towards increasing the stability of the plate.

FIG. 2 shows that the proximal end 8, in contrast to the distal end 9, has a spoon-like shape, i.e. is arched. As a result, the osteosynthesis plate 1b can be used both for the left and for the right proximal humerus. Owing to this arched, spoon-like design, however, it is precisely these bending loads as discussed above that occur. The relief notch is therefore extremely useful especially in the case of such osteosynthesis plates.

The notch 5 is a recess which is introduced into the osteosynthesis plate. It can otherwise be described using the terms "incision" or "groove". The notch 5 is in particular rounded in order to reduce the influence of the notch effect.

The depth of the notch 5 depends on the curvature of the osteosynthesis plate 1. The greater this curvature, the deeper it is possible to form the notch. The side view of a plate may serve as an aid for determining the preferred depth of the notch 5. If, in side view, as shown in FIG. 2A, the web 12 present between the drilled holes 4, 4' no longer projects beyond the edge of the drilled holes, the notch 5 has the preferred depth. The curvature of the plate should conceal the notch in side view.

In other words, the notch 5 has a depth which substantially corresponds to the depth of the edge 15, 15' and 17, 17' of the drilled hole 4, 4' and 2, 2', respectively, which depth is present in that region 19, 19' or 18, 18' of the drilled hole 4, 4' or 2, 2', respectively, which is transverse to the longitudinal axis of the notch 5 and which is further away from the notch. The notch is consequently preferably approximately as deep as the depth of the opposite edge of the drilled hole, which is clearly evident in particular from FIG. 1A and FIG. 2A. The "depth" of the edge of the drilled hole is understood thereby as meaning the distance between the edge of the drilled hole and the plane which lies on the top of the osteosynthesis plate. This definition also makes it clear that the depth is dependent on the curvature of the plate, the spacing of the drilled holes between which the notch is made and the thickness of the plate. However, the depth may vary. What is important, however, is that the notch is only so deep that no new exposed zone is produced, for example, on the outside of the drilled holes (in FIG. 2, in the region of reference numeral 10, 10').

As mentioned above, the notch 5 is made between two drilled holes arranged adjacent to one another. In an embodiment, the notch 5 extends coaxially with a straight line 14 which connects the two midpoints 13, 13' of the drilled holes 2, 2', as shown in FIG. 1B. The longitudinal axis of the notch 1a consequently coincides with the straight line 14. In the case of special plate forms, in particular curved osteosynthesis plates, the notch 5 may be displaced from the middle of the web. Thus, it is intended that the relief notch be displaced parallel to this connection of the midpoints, as shown, for example, in FIG. 2B. Here, the notch 5b has been displaced in the direction towards the proximal end 8 of the osteosynthesis plate 1b. The notch 5b forms the tangent to the two drilled holes 4, 4'. It is advantageous if the proximal region of the edge 16 of the notch 5 is approximately at the height at which the proximal region of the edge 15, 15' of the drilled hole 4, 4' is present, or above this height. This ensures the load distribution.

As is evident in particular from FIG. 2, the notch 5 is arranged transversely to the longitudinal axis 3 of the osteosynthesis plate 1b.

The drilled holes between which the notch is arranged are arranged adjacent to one another. Here, "adjacent" is understood as meaning that the drilled holes are comparatively close together. The exact magnitude of the distance between the adjacent drilled holes at which the present invention displays its advantageous effects depends in turn on the curvature of the osteosynthesis plate. Moreover, the size of the implant is decisive. Furthermore, it depends to a certain degree also on the total number of drilled holes arranged on the implant. In any case, two drilled holes are arranged adjacent to one another in the context of the invention if only a narrow web which leads to excess stresses at this point remains between them.

The two drilled holes 2, 2' or 4, 4' can also be regarded as being adjacent in the context of the invention if their spacing is not so great that the above-defined depth of the notch 5 exceeds the thickness of the osteosynthesis plate 1. This means that the distance between the drilled holes 2, 2' or 4, 4' arranged adjacent to one another depends on the depth of the notch 5 in that the notch is not deeper than the thickness of the osteosynthesis plate 1. If the depth of the notch 5 is therefore adapted to the depth of the opposite edge 15, 15' or 17, 17' in the case of a curved osteosynthesis plate 1 at some time a point will be reached at which this edge 15, 15' or 17, 17' is present below a plane defined by the bottom of the plate, i.e. is lower than the bottom of the plate. If the notch 5 were then still to be as deep as the edge 15, 15', 17, 17', this depth would be greater than the thickness of the plate and the latter consequently broken through. It is also clear therefrom that the spacing of the drilled holes in the case of more greatly curved plates will be smaller than in the case of plates having a smaller curvature. Here, the drilled holes between which the notch according to the invention is made may be further apart, and the notch can nevertheless perform its function according to the invention.

LIST OF REFERENCE NUMERALS

1—Osteosynthesis plate
2—Drilled hole
3—Longitudinal axis
4—Drilled hole
5—Notch
6—Convex side 7—Concave side
8—Proximal end
9—Distal end
10—Lateral web
11—Arrow
12—Web
13—Midpoint
14—Straight line
15—Edge
16—Edge
17—Edge
18—Region
19—Region

The invention claimed is:

1. An osteosynthesis plate comprising:
a plate body having a convex surface and a concave surface, the convex and concave surfaces defining a plate thickness extending between the convex and concave surfaces;
first and second fastener holes passing through the plate body from the convex surface to the concave surface, the first fastener hole having a first perimeter at the convex surface, and the second fastener hole having a second perimeter at the convex surface; and
a notch formed in the convex surface and extending toward, but not penetrating, the concave surface, the notch disposed between the first and second fastener holes and overlapping with at least a portion of both the first and second perimeters of the first and second fastener holes, a depth of the notch extending from the convex surface to a plane connecting opposing edges of the first and second fastener holes on the convex surface farthest away from one another.

2. The osteosynthesis plate of claim 1, wherein the notch has a longitudinal axis that substantially coincides with a straight line formed by midpoints of the first and second fastener holes.

3. The osteosynthesis plate of claim 1, wherein the notch has a longitudinal axis that is parallel to and displaced from a straight line formed by midpoints of the first and second fastener holes.

4. The osteosynthesis plate of claim 3 wherein the notch forms a tangent to the first and second fastener holes.

5. The osteosynthesis plate of claim 1, wherein the notch comprises a proximal region, wherein the first and second fastener holes each comprise a proximal region, and wherein the proximal region of the notch has a height that is equal to or greater than the height of the proximal region of the first and second fastener holes.

6. The osteosynthesis plate of claim 1, wherein the notch is rounded.

7. The osteosynthesis plate of claim 1, wherein the notch is arranged transversely to the longitudinal axis of the osteosynthesis plate.

8. The osteosynthesis plate of claim 1, wherein the proximal part of the osteosynthesis plate is arched in a spoon-like manner so that the osteosynthesis plate can be used both for the left and for the right proximal humerus.

9. An osteosynthesis plate having a convex side, wherein a proximal part of the osteosynthesis plate is arched in a spoon-like manner so that the osteosynthesis plate can be used both for the left and for the right proximal humerus, the osteosynthesis plate comprising:
first and second fastener holes arranged adjacent to one another, each fastener hole having an edge; and
a notch having a longitudinal axis and disposed between the first and second fastener holes on the convex side of the osteosynthesis plate, the longitudinal axis being parallel to and displaced from a straight line formed by midpoints of the first and second fastener holes, wherein a depth of the notch extends from the convex surface to a plane extending parallel to a longitudinal axis of the plate and connecting opposing edges of the first and second fastener holes on the convex surface farthest away from one another.

10. The osteosynthesis plate of claim 1, wherein the depth of the notch further corresponds to a distance between the first and second fastener holes.

11. The osteosynthesis plate of claim 1, wherein the plane extends parallel to a longitudinal axis of the plate.

* * * * *